United States Patent
Brand et al.

(10) Patent No.: US 11,355,235 B2
(45) Date of Patent: Jun. 7, 2022

(54) METHOD AND DEVICE FOR REMOTE MONITORING AND CONTROL OF MEDICAL FLUID MANAGEMENT DEVICES

(75) Inventors: Georg Brand, Wuerzburg (DE); Daniel Hauck, Sulzheim (DE); Peter Kloeffel, Nuedlingen (DE); Thomas Stahl, Esselbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 548 days.

(21) Appl. No.: 13/549,628

(22) Filed: Jul. 16, 2012

(65) Prior Publication Data
US 2013/0018355 A1    Jan. 17, 2013

Related U.S. Application Data

(60) Provisional application No. 61/457,947, filed on Jul. 15, 2011.

(30) Foreign Application Priority Data

Jul. 15, 2011   (DE) .................. 10 2011 107 795.6

(51) Int. Cl.
*G16H 40/67* (2018.01)
*G16H 20/40* (2018.01)

(52) U.S. Cl.
CPC ............. *G16H 40/67* (2018.01); *G16H 20/40* (2018.01)

(58) Field of Classification Search
CPC ........... G06F 17/3089; G06F 17/30905; G06F 17/30902; G06F 17/30241;
(Continued)

(56) References Cited

U.S. PATENT DOCUMENTS 5,472,614 A    12/1995  Rossi
5,664,084 A *   9/1997  Smith ..................... G01S 7/064
                                                    345/440
(Continued)

FOREIGN PATENT DOCUMENTS

DE       197 42 633 A    4/1999
DE       198 23 240 A1   12/1999
(Continued)

OTHER PUBLICATIONS

Application Document, "Bluetooth Secure Simple Pairing Using NFC," Bluetooth Special Interest Group, NFC Forum, NFCForum-AD-BTSSP-1.0, Oct. 18, 2011, 32 pages.
(Continued)

*Primary Examiner* — Tonia L Dollinger
*Assistant Examiner* — Joseph M Cousins
(74) *Attorney, Agent, or Firm* — Fish & Richardson P.C.

(57) ABSTRACT

A method and device that relates to the field of medical fluid management devices, in particular dialysis machines, provided. The method and device is configured to provide for the monitoring and control of medical fluid management devices from a remote site. To do so, the screen content of the output device of a fluid management device is transmitted at least partially to an output device of a remote control unit. The screen content optionally has user interfaces, which can be selected on the remote control device and lead to changes in the control of the transmitting medical fluid management device.

17 Claims, 5 Drawing Sheets

(58) Field of Classification Search
CPC . H04L 29/06047; H04L 67/02; H04L 67/025;
H04L 67/12; H04L 67/18; H04L 69/329;
G06Q 30/02; H04W 4/02; H04W 4/185
USPC ......................................................... 709/203
See application file for complete search history.

(56) References Cited

U.S. PATENT DOCUMENTS

| | | | |
|---|---|---|---|
| 6,385,728 B1 | 5/2002 | Debry | |
| 6,673,314 B1 | 1/2004 | Burbank et al. | |
| 6,676,621 B1 | 1/2004 | Menninger | |
| 7,033,539 B2 | 4/2006 | Krensky et al. | |
| 7,044,927 B2 | 5/2006 | Mueller et al. | |
| 7,078,911 B2 | 7/2006 | Cehelnik | |
| 7,300,418 B2 | 11/2007 | Zaleski | |
| 7,539,533 B2 | 5/2009 | Tran | |
| 7,699,806 B2 | 4/2010 | Ware et al. | |
| 7,981,281 B2 | 7/2011 | Yu et al. | |
| 8,190,651 B2 | 5/2012 | Treu et al. | |
| 8,313,642 B2 | 11/2012 | Yu et al. | |
| 8,315,885 B2 | 11/2012 | Krogh et al. | |
| 8,332,503 B2* | 12/2012 | Takagi | H04L 12/2602 709/203 |
| 8,449,471 B2 | 5/2013 | Tran | |
| 8,487,881 B2 | 7/2013 | Keenan | |
| 8,529,496 B2 | 9/2013 | Britton et al. | |
| 8,532,343 B1* | 9/2013 | Freedman | G06K 9/00335 382/115 |
| 8,549,600 B2 | 10/2013 | Shedrinsky | |
| 8,566,601 B1 | 10/2013 | Waters | |
| 8,776,246 B2 | 7/2014 | Allegri et al. | |
| 8,871,095 B2 | 10/2014 | Yu et al. | |
| 8,905,959 B2 | 12/2014 | Basaglia | |
| 8,909,613 B2 | 12/2014 | Treu et al. | |
| 8,970,503 B2 | 3/2015 | Christie et al. | |
| 8,996,393 B2 | 3/2015 | Sobie | |
| 9,050,411 B2 | 6/2015 | Kelly et al. | |
| 9,178,891 B2 | 11/2015 | Wang et al. | |
| 9,251,310 B2 | 2/2016 | McNally et al. | |
| 9,514,283 B2 | 12/2016 | Childers et al. | |
| 9,582,645 B2 | 2/2017 | Yu et al. | |
| 9,675,745 B2 | 6/2017 | Kelly et al. | |
| 9,690,905 B2 | 6/2017 | Yu et al. | |
| 9,697,334 B2 | 7/2017 | Yu et al. | |
| 9,800,663 B2 | 10/2017 | Arrizza | |
| 9,861,733 B2 | 1/2018 | Burbank et al. | |
| 10,173,008 B2 | 1/2019 | Simpson et al. | |
| 2002/0198473 A1 | 12/2002 | Kumar | |
| 2003/0158823 A1 | 8/2003 | Fulton et al. | |
| 2004/0088541 A1 | 5/2004 | Messerges et al. | |
| 2004/0111294 A1 | 6/2004 | McNally et al. | |
| 2004/0117643 A1 | 6/2004 | Lakamp et al. | |
| 2004/0193413 A1 | 9/2004 | Wilson et al. | |
| 2005/0055244 A1 | 3/2005 | Mullan | |
| 2005/0085760 A1* | 4/2005 | Ware | A61M 1/3441 604/4.01 |
| 2005/0097191 A1* | 5/2005 | Yamaki et al. | 709/219 |
| 2005/0277911 A1* | 12/2005 | Stewart | A61M 5/142 604/890.1 |
| 2006/0052676 A1* | 3/2006 | Wang | G16H 40/67 600/300 |
| 2006/0200260 A1 | 9/2006 | Hoffberg et al. | |
| 2006/0271409 A1* | 11/2006 | Rosenfeld | G08B 25/08 705/3 |
| 2007/0143782 A1 | 6/2007 | Lakamp et al. | |
| 2007/0150517 A1* | 6/2007 | Malone | H04L 9/3263 |
| 2007/0198001 A1* | 8/2007 | Bauch | G16H 40/63 606/1 |
| 2007/0256615 A1* | 11/2007 | Delgrosso | E05G 1/08 109/38 |
| 2007/0266443 A1 | 11/2007 | Wilson et al. | |
| 2008/0004601 A1* | 1/2008 | Jennewine et al. | 604/890.1 |
| 2008/0104615 A1* | 5/2008 | Nolan | G16H 10/60 719/328 |
| 2008/0114226 A1 | 5/2008 | Music et al. | |
| 2008/0139898 A1 | 6/2008 | Johnson et al. | |
| 2009/0125147 A1* | 5/2009 | Wang | G06T 7/0012 700/264 |
| 2009/0259960 A1 | 10/2009 | Steinle et al. | |
| 2009/0275881 A1 | 11/2009 | Lo et al. | |
| 2009/0303204 A1 | 12/2009 | Nasir | |
| 2010/0066676 A1 | 3/2010 | Kramer et al. | |
| 2010/0114639 A1 | 5/2010 | Leiendecker et al. | |
| 2010/0121654 A1* | 5/2010 | Portnoy | G06F 19/325 705/3 |
| 2010/0137693 A1* | 6/2010 | Porras | A61M 1/16 600/301 |
| 2010/0138534 A1 | 6/2010 | Mutnuru et al. | |
| 2010/0200506 A1 | 8/2010 | Ware | |
| 2011/0001605 A1* | 1/2011 | Kiani | G16H 30/20 340/5.6 |
| 2011/0037586 A1* | 2/2011 | Lu | G06F 19/327 340/539.1 |
| 2011/0066006 A1 | 3/2011 | Banet et al. | |
| 2011/0093294 A1 | 4/2011 | Elahi et al. | |
| 2011/0106557 A1* | 5/2011 | Gazula | G16H 80/00 705/3 |
| 2011/0157480 A1 | 6/2011 | Curl | |
| 2011/0164163 A1 | 7/2011 | Bilbrey et al. | |
| 2011/0169644 A1* | 7/2011 | Muhsin | G08B 25/008 340/573.1 |
| 2011/0170692 A1* | 7/2011 | Konrad | H04L 9/0825 380/260 |
| 2011/0173308 A1* | 7/2011 | Gutekunst | 709/222 |
| 2011/0193704 A1* | 8/2011 | Harper | A61B 5/14532 340/573.1 |
| 2011/0213225 A1* | 9/2011 | Bernstein et al. | 600/309 |
| 2011/0270974 A1* | 11/2011 | Burdette et al. | 709/224 |
| 2011/0282168 A1* | 11/2011 | Weiss et al. | 600/323 |
| 2011/0307284 A1* | 12/2011 | Thompson et al. | 705/7.13 |
| 2011/0319056 A1* | 12/2011 | Toy et al. | 455/412.2 |
| 2012/0001751 A1* | 1/2012 | Baker | A61B 5/7285 340/539.12 |
| 2012/0003933 A1 | 1/2012 | Baker et al. | |
| 2012/0108999 A1* | 5/2012 | Leininger | A61B 5/0004 600/546 |
| 2012/0116218 A1* | 5/2012 | Martin | A61B 8/4405 600/437 |
| 2012/0138533 A1 | 6/2012 | Curtis et al. | |
| 2012/0306994 A1* | 12/2012 | Schwartz | G16H 40/67 348/14.08 |
| 2013/0138452 A1 | 5/2013 | Cork et al. | |
| 2013/0141329 A1 | 6/2013 | Halbert et al. | |
| 2013/0249855 A1 | 9/2013 | Zhang | |
| 2013/0310726 A1 | 11/2013 | Miller et al. | |
| 2013/0318357 A1 | 11/2013 | Abraham et al. | |
| 2013/0346102 A1 | 12/2013 | Yu et al. | |
| 2014/0006510 A1 | 1/2014 | Hamilton et al. | |
| 2014/0121845 A1 | 5/2014 | Mueller | |
| 2014/0152466 A1* | 6/2014 | Wiesner | A61B 5/0026 340/870.07 |
| 2014/0188516 A1 | 7/2014 | Kamen | |
| 2014/0266983 A1 | 9/2014 | Christensen | |
| 2014/0267003 A1 | 9/2014 | Wang | |
| 2014/0276375 A1 | 9/2014 | Minkus | |
| 2014/0288947 A1 | 9/2014 | Simpson et al. | |
| 2014/0371816 A1* | 12/2014 | Matos | B60W 40/09 607/59 |
| 2015/0011970 A1 | 1/2015 | Kamen et al. | |
| 2015/0095041 A1 | 4/2015 | Kim | |
| 2015/0253860 A1 | 9/2015 | Merics et al. | |
| 2015/0332004 A1 | 11/2015 | Najafi | |
| 2015/0370973 A1 | 12/2015 | Jones | |
| 2016/0206800 A1 | 7/2016 | Tanenbaum et al. | |
| 2016/0261974 A1 | 9/2016 | Arrizza | |
| 2017/0076069 A1 | 3/2017 | Moissl et al. | |

(56) References Cited

U.S. PATENT DOCUMENTS

| | | |
|---|---|---|
| 2017/0087290 A1 | 3/2017 | Medina et al. |
| 2018/0036469 A1 | 2/2018 | Crnkovich et al. |

FOREIGN PATENT DOCUMENTS

| | | |
|---|---|---|
| DE | 198 49 787 | 2/2000 |
| DE | 19845027 | 4/2000 |
| DE | 10 2004 011 168 A1 | 9/2004 |
| DE | 10 2007 058 890 A1 | 6/2008 |
| DE | 202012005295 | 9/2012 |
| DE | 102012020945 | 4/2014 |
| EP | 2145451 | 1/2010 |
| EP | 2237131 | 10/2010 |
| GB | 2368435 | 5/2000 |
| WO | WO 2007/126360 | 11/2007 |
| WO | WO 2008/042219 | 4/2008 |
| WO | WO 2008/144325 | 11/2008 |
| WO | WO 2009/122270 | 10/2009 |
| WO | WO 2011/028261 | 3/2011 |
| WO | WO 2014/004448 | 1/2014 |
| WO | WO 2015/134229 | 9/2015 |

OTHER PUBLICATIONS

Hsu et al., "A security and privacy preserving e-prescription system based on smart cards," Journal of Medical Systems, Mar. 2012, 36(3):3637-3647.

Jung et al., "Interoperability between Medical Devices using Near Field Communication", IEEE, Jun. 24, 2013, pp. 1-4.

PCT International Preliminary Report on Patentability in International Appln. No. PCT/EP2012/002872, dated Jan. 21, 2014, 8 pages.

PCT International Preliminary Report on Patentability in International Appln. No. PCT/US2017/042111, dated Feb. 5, 2019, 13 pages.

PCT International Preliminary Report on Patentability in International Appln. No. PCT/US2018/027857, dated Oct. 29, 2019, 10 pages.

PCT International Search Report and Written Opinion in International Appln. No. PCT/US2016/019331, dated May 31, 2016, 13 pages.

PCT International Search Report and Written Opinion in International Appln. No. PCT/US2017/042111, dated Nov. 15, 2017, 21 pages.

PCT International Search Report and Written Opinion in International Appln. No. PCT/US2018/027857, dated Jun. 29, 2018, 15 pages.

PCT International Search Report in International Appln. No. PCT/EP2012/002872, dated Dec. 6, 2012, 3 pages.

PCT Invitation to Pay Additional Fees in International Appln. No. PCT/US2017/042111, dated Sep. 15, 2017, 12 pages.

Pennsylvania Patient Safety Advisory, "Hemodialysis Administration: Strategies to Ensure Safe Patient Care," retrieved from URL <http://patientsafety.pa.gov/ADVISORIES/documents/201009_87.pdf>, Jan. 1, 2010, 11 pages.

* cited by examiner

METHOD AND DEVICE FOR REMOTE MONITORING AND CONTROL OF MEDICAL FLUID MANAGEMENT DEVICES

This application claims the benefit of U.S. provisional application No. 61/457,947, filed Jul. 15, 2011, and priority of German number 10 2011 107 795.6 filed Jul. 15, 2011, hereby incorporated by reference.

BACKGROUND OF THE INVENTION

1. Field of the Invention

The invention relates to a method and a device for remote monitoring and control of medical fluid management devices.

DESCRIPTION OF THE RELATED ART

Medical fluid management devices are understood here to refer in particular to devices for conducting, treating and/or distributing liquids and/or gases in which fluid is conveyed between a patient and a fluid treatment component and/or a fluid source through a fluid line.

Fluid management devices are also understood in particular to include fluid treatment devices such as blood treatment devices in which a fluid from a patient is sent through a fluid line to a fluid treatment component, is treated by the fluid treatment component and returned to the patient through the fluid line which can be divided into an arterial branch and a venous branch. Examples of such blood treatment devices include in particular hemodialysis machines. One such blood treatment device is the subject matter of DE 198 49 787 C1 by the present applicant.

Dialysis is a method for purifying the blood of patients who have acute or chronic renal insufficiency. Essentially a distinction is made here between methods having an extracorporeal blood circulation such as hemodialysis, hemofiltration or hemodiafiltration (combined below under the term hemodialysis) and peritoneal dialysis which does not involve any extracorporeal blood circulation.

In hemodialysis the blood is conveyed through the blood chamber of a dialysis machine in an extracorporeal circulation, which is separated from the dialysis liquid chamber by a semipermeable membrane. A dialysis fluid containing the blood electrolytes in a certain concentration flows through the dialysis fluid chamber. The substance concentration of the dialysis fluid corresponds to the concentration of the blood of a healthy patient. During the treatment the patient's blood and the dialysis fluid are passed by both sides of the membrane in general in countercurrent with a predetermined flow rate. The substances that must be eliminated in the urine diffuse through the membrane from the blood chamber into the chamber for dialysis fluid while at the same time electrolytes present in the blood and in the dialysis fluid diffuse from the chamber with the higher concentration to the chamber with the lower concentration. If a pressure gradient is built up from the blood side to the dialyzate side on the dialysis membrane, for example, by a pump, which withdraws dialyzate from the dialyzate circulation downstream from the dialysis filter on the dialyzate side, water goes from the patient's blood through the dialysis membrane into the dialyzate circulation. This ultrafiltration process results in the desired removal of water from the patient's blood.

In hemofiltration, ultrafiltrate is withdrawn from the patient's blood by applying a transmembrane pressure in the dialysis machine without passing the dialysis fluid by the dialysis machine membrane on the side of the dialysis machine membrane opposite the patient's blood. In addition, a sterile and pyrogen-free substituate solution may be added to the patient's blood. Depending on whether this substituate solution is added upstream or downstream from the dialysis machine, we speak of predilution or postdilution, respectively. the mass exchange takes place by convection in hemofiltration.

Hemodiafiltration combines the methods of hemodialysis and hemofiltration. A diffuse mass exchange takes place between the patient's blood and the dialysis fluid through the semipermeable membrane of a dialysis machine as well as filtering of plasma water through a pressure gradient on the membrane of the dialysis machine.

Plasmapheresis is a method by which the patient's blood is separated into the blood plasma and its corpuscular components (cells). The separated blood plasma is purified or replaced by a substitution solution and returned to the patient.

In peritoneal dialysis the abdominal cavity of a patient is filled with a dialysis fluid through a catheter guided through the abdominal wall such that the dialysis fluid has a concentration gradient with respect to the endogenous fluids. The toxins present in the body enter the abdominal cavity through the peritoneum which acts as a membrane. After a few the dialysis fluid in the patient's abdominal cavity is replaced. By osmotic processes water can be transferred from the patient's blood through the peritoneum into the dialysis fluid, thereby removing the water from the patient's body.

Dialysis methods are usually performed with the help of automatic dialysis machines such as those distributed by the applicant under the designation 5008 or sleep.safe.

These dialysis machines are complex medical fluid management systems with extensive functions, the operation and monitoring of which often requires specially trained personnel, in particular for hemodialysis machines.

In hemodialysis, it has become standard practice to treat patients in dialysis centers, clinics or special dialysis practices, where several dialysis machines are kept, so that several patients can be treated simultaneously.

Trained medical personnel is responsible for equipping the machines with the required disposable medical articles such as tube sets, dialysis filters and medical solutions and/or concentrates and they set the machine individually for each patient according to the doctor's instructions. Likewise the patient is connected to the dialysis machine and monitored constantly during dialysis by the safety equipment of the dialysis machine and by the medical personnel.

For operator input and for information output, dialysis machines are often equipped with touchscreens. The applicant's patent DE 197 426 33 A gives an example of this.

Dialysis machines may be equipped with extensive functions for monitoring the treatment and the patient. For example, the pressure in the arterial blood tube carrying blood from the patient to the dialysis machine can be monitored. An excessive drop in the arterial blood pressure may indicate that the arterial needle has been disconnected, for example, or it may indicate that the arterial needle is applying suction to the patient's vascular wall. Either case justifies alarming the medical personnel which must then perform additional steps.

However, situations may also occur with machines for automatic peritoneal dialysis which is often performed at the patient's home but not necessarily, but such situations may necessitate an operator intervention by a skilled person such as a dialysis nurse or a dialysis physician.

If the dialysis machine is at the patient's home, as is often the case in peritoneal dialysis, manual intervention by medical personnel is impossible.

In a dialysis practice or in a dialysis clinic, several dialysis machines are usually located in one room and there are often multiple dialysis machines in different rooms which are at a distance from one another or may even be distributed over various floors.

An alarm state is often signaled acoustically and optically by a dialysis machine to draw the attention of the medical personnel to a corresponding incident, for example, in the style of a traffic light.

Independently of this however, alarm states are often signaled acoustically by alarm tones or alarm tone sequences which must have a prescribed loudness in order for the medical personnel to be reliably alerted.

Such acoustic alarms are therefore also heard by other patients who are being treated in the same room, which may be perceived as annoying. The dialysis treatment usually lasts for several hours. The patient's often sleep during the dialysis treatment so that an acoustic alarm also causes the patient to be awakened. Therefore the European standard for electrical medical devices DIN EN 60601-2-16 stipulates the possibility of a remote alarm for the medical personnel by having the alarm initially output only at a remote device.

If an alarm state occurs, the medical personnel must move to the machine sending out the alarm in order to evaluate the cause of the alarm and eliminate it. The medical personnel must also approach the patient and the dialysis machine for regularly checking on the machine and the patient's wellbeing. The medical personnel is often also summoned by the patient himself when he has a concern.

In daily dialysis practice this means relatively great distances for the medical personnel and increased agitation in the treatment rooms, which should be avoided from the standpoint of comfort and for therapeutic reasons.

In addition, it may happen that a medical intervention in the control of the dialysis machine is necessary. However, physicians are not necessarily constantly present in spatial proximity to the patients. In such a case valuable time may elapse under some circumstances before a medical intervention is performed.

SUMMARY OF THE INVENTION

The object of the present invention is to design methods and devices so that the monitoring and control of medical fluid management equipment are possible from a remote location and their safety and operating convenience are increased.

These objects are achieved according to the invention by a method for remote monitoring and control of medical fluid management equipment having at least one input and output device which is preferably a touchscreen display. According to the method, a data transmission takes place in which at least part of the information content of the leant one input and output device of a medical fluid management device is transmitted and output to at least one remote control unit. An operator input can be input on at least one input and output device of the at least one remote control unit, also preferably a touchscreen, to remotely control the medical fluid management device.

The objects are also achieved by a medical fluid management device having at least one input and output device preferably touchscreen display, and at least one remote control unit having at least one input and output device, also preferably a touchscreen display. The medical fluid management device and the remote control unit are equipped to transmit data, such that at least a part of the information content of the at least one input and output device of the medical fluid management devices is transmitted to at least one remote control unit, and the remote control unit is equipped to display the information content transmitted from the medical fluid management device on the at least one input and output device and to transmit operator input on the at least one input and output device of the remote control unit to the medical fluid management device.

The invention is based on a method for remote monitoring and control of medical fluid management devices having at least one input and output device, preferably a touchscreen display, where at least parts of the information content of the at least one input and output device of the medical fluid management equipment are to be transferred to at least one remote control unit and output, and operator input can be entered on at least one input and output device of the remote control unit preferably a touchscreen, controlling a medical fluid management device.

In addition, the invention is based on a medical fluid management device having at least one input and output device, preferably a touchscreen display and a remote control unit having at least one input and output device, preferably a touchscreen display, where the medical fluid management device is equipped to transfer at least parts of the information content of the at least one input and output device of the medical fluid management device to at least one remote control unit, and the remote control unit is equipped to display the information content transferred from the medical fluid management device to the at least one input and output device and to transfer operator input at the at least one input and output device to the medical fluid management device.

A dialysis machine which may be embodied as a hemodialysis machine or as a device for automatic peritoneal dialysis is described below as representative of a medical fluid management device. It will be clear to those skilled in the art that the invention can readily be applied to any medical fluid management device.

Dialysis machines are often equipped with touchscreen user interfaces, which serve as input and output devices. Technical medical equipment furnished with touchscreens provide the operator with a comfortable, variable user interface which is also hygienic due to the flat an uninterrupted surface.

Variable image contents can be displayed on the touchscreen through software control. Thus the settings of the dialysis machines, for example, the dialysis fluid flow rate or the elapsed dialysis time can be displayed on the touchscreen. Current measured values, for example, the arterial and venous pressure in the access tubes can also be displayed. By touching the touchscreen at operator areas, operator input for the dialysis machine can be made to alter the settings of the dialysis machine, for example, or to respond to an alarm appropriately.

According to the invention the image content of the dialysis machine is transferred to a remote control unit. This transfer may take place by a hard-wired connection, e.g., via a local area network (LAN) or wirelessly, for example, by radio (WLAN, Bluetooth) or by optical transmission, for example, by infrared interface.

The remote control unit is preferably also equipped with a touchscreen but in any case with a display screen and an input device such as a keyboard and/or a computer mouse.

The image content transferred from the dialysis machine is output on the output device on the remote control unit. Thus there is a one-to-one image of image content of the touchscreen of the dialysis machine sending the information. If the input and output device of the remote control unit is designed as a touchscreen, then operator input on the control unit may be done here like operator input on the dialysis machine. There is then no difference in operation between the dialysis machine and the remote control unit.

However, the remote control unit may also be designed without a touchscreen, for example, as a notebook with a touchpad or a connected computer mouse. The software of the remote control unit in this case is programmed so that operator input can be implemented via the keyboard and/or via the touchpad and/or via the computer mouse. For example, numerical entries which may be entered by finger pressure on the touchscreen on the dialysis machine via a numerical keypad which is displayed and may be entered conveniently and rapidly by keyboard on a notebook.

The remote control unit may also be a smartphone or a tablet PC in particular a mobile computer which may be carried by physicians or other medical personnel.

For all embodiments of the remote control unit it is essential that the operator input on user interfaces of the screen content sent by the sending dialysis machine is transmitted to the input and output device of the remote control unit on each dialysis machine which sent the screen contents where they manifest the same effect as if they had been input on this dialysis machine.

The monitoring and control of dialysis machines from a remote control unit is possible in real time in this way, and in a particularly advantageous manner it is possible from any location within the range of the network over which the dialysis machines and the remote control unit communicate with one another.

If this communication takes place not only between a dialysis machine and a remote control unit but also between a dialysis machine and multiple remote control units, then prioritization of the operator input at the remote control units may be performed by assigning a priority to the remote control units based on the qualification of the operator.

For example, a lower priority may be assigned to a remote control unit which is near a nurse's room than to a remote control unit operated by a dialysis physician. Operator input from a remote control unit of a high priority is then executed preferentially in comparison with operator input from a remote control unit of a lower priority.

For example, if the dialysis physician has stopped a dialysis treatment by means of a remote control unit which can be assigned to him, then a dialysis nurse cannot readily resume this treatment via an operator input on a remote control unit which may be assigned to her.

The assignment of the remote control units may be done, for example, via network address or device-specific hardware address (MAC address) and stored allocation tables or by using a PKI system (PKI, English for public key infrastructure) which can issue, distribute and verify digital certificates. Alternatively or additionally the operating personnel at the remote control unit may provide authentication in a suitable manner, for example, by entering a personal user name and password combination (personal alphanumeric code) or by entering the fingerprint via a fingerprint sensor or by entering an eye iris scan.

It is possible in this way to be sure that only authorized persons are allowed to operate the dialysis machine and that operator input by people of a higher professional competence than people of a lower professional competence is executed in a preferential manner.

Another embodiment of the invention provides that in addition to transmitting the information content of the at least one input and output device of a dialysis machine, video and audio signals can also be exchanged by people.

To this end, at least the dialysis machines, preferably also the remote control units, are equipped with a camera and/or a loudspeaker and/or a microphone.

The camera on the dialysis machine is preferably aimed at the dialysis patient. In case of need the instantaneous image of the patient is transmitted to the remote control unit where it is displayed. In this way the medical personnel can see the respective patient.

The remote control unit may also be equipped with a camera and/or a loudspeaker and/or a microphone to display the image of the medical personnel on the display screen of a dialysis machine and/or to enable verbal communication.

The camera images are preferably displayed on partial areas of the output devices.

Visual or verbal and/or acoustic communication may be initiated here by the dialysis machine as well as by the remote control unit in that a corresponding operating measure is performed on the device itself or on an external device connected to the dialysis machine, such as a remote control or a patient interface.

The patient and physician and/or medical personnel can speak to one another in this way and can both see the respective display screen. For example, dialysis patients can inform the medical personnel of their needs without having to wait for the medical personnel to come close enough to call. Conversely, the medical personnel can speak to a patient, for example, to ask him how he is doing without having to move him.

This means a great relief in terms of labor and eliminates unnecessary distances in a treatment ward, which makes a significant contribution toward restfulness and comfort in the treatment ward.

There can be communication through a camera, a microphone and a loudspeaker not only between medical personnel and the patient or limited to two participants. For example, communication among patients themselves is also conceivable. It may happen during the work sequence of a dialysis ward that patients who have become friends and are treated at the same time are treated at dialysis machines located a great distance apart from one another.

Due to the inventive embodiment of the dialysis machines with camera, loudspeaker and microphone, the patients can also communicate with one another. For such communication it is advantageous if the dialysis machines are additionally equipped with a mobile portable patient interface which is reserved for the dialysis patient. Such a patient interface may be, for example, a notebook or a tablet PC which is preferably connected wirelessly to the dialysis machine or to a remote server for technical data transmission and can be unambiguously assigned to the treatment site. The output device of the mobile portable patient interface is preferably a touchscreen.

The mobile patient interface may also be equipped with a camera and/or loudspeaker and/or microphone. The dialysis machine is usually set up so that the output device can be read conveniently by the medical personnel. This often means that the patient being treated has little or no view of the output device of the dialysis machine. The information on the output device of the dialysis machine is often of no interest for the patient.

If the patient interface is defined as a portable device, the patient can hold the patient interface conveniently during dialysis so that the output device is readily readable. The image content of the output device of the patient interface may be independent of the image content of the output device of the dialysis machine. Thus, for example, multimedia contents such as movies or images may be displayed, but a web browser enabling access to the Internet is also conceivable. The patient is thus entertained and informed individually during the dialysis treatment. So as not to interfere with other patients in a dialysis ward, the patient interface may be equipped with headphones.

For communication between patients, special software may be provided, listing all the patients participating in the patient-to-patient communication somewhat like an exchange. It is conceivable for a selection window on which the patient can establish a connection for the purpose of communication with other patients by user input through appropriate user input on a patient interface.

Another inventive embodiment provides that the remote control unit is a smartphone which the medical personnel in particular a physician carries with him. Smartphones are characterized by their expanded computer functionality in comparison with normal mobile telephones. This may be manifested, for example, in a high resolution display, preferably with a touchscreen functionality. The operating systems of smartphones are usually designed so that a variety of program so-called apps can be executed. Smartphone devices are understood to include all modern devices having a computer functionality in the sense of the invention but not being computers in the sense of laptops or notebooks, for example, even so-called tablet PCs.

Smartphones usually exchange data over the mobile communications network as well as over local radio networks (WLAN, Bluetooth). A physician carrying such a smartphone can have access to a certain display unit from anywhere in the manner described above. Smartphones are usually also equipped with a camera so that direct communication with image transmission in the manner described here is also possible with this embodiment.

This embodiment is especially advantageous in patients who undergo so-called hemodialysis, for example, in peritoneal dialysis or with hemodialysis machines for home use. In such cases, the patient performs the dialysis at home and usually there is no medical personnel on hand. However, then situations in which expert intervention in the control of the device may be necessary may occur. According to the invention such an intervention may be performed now by the medical personnel via the remote control which may be a smartphone. In addition, communication in the manner already described may also take place via the mobile communications network or via the Internet.

It is essential for the security of the remote control of a dialysis machine that there is no faulty transmission of image data from the dialysis machine to the remote control unit and/or faulty transmission of operator input from the remote control unit to the dialysis machine.

Extensive safety measures are taken in this regard. It is provided that the image content of a dialysis machine is periodically transferred to the remote control unit. Thus there is a periodic screen update. In addition, screen updates may be performed when the image content changes, for example, when a measured value displayed on the display screen of the dialysis machine changes.

To be sure that the image transmitted to the remote control unit has the same content as that on the dialysis machine, a CRC (cyclic redundancy check) of the screen content may also be calculated and transmitted with each screen update. The cyclic redundancy check (CRC) is a method for determining a check value for data to be able to detect errors in the transmission or storage. In the remote control unit, a CRC may also be calculated for the received screen content and compared with the received CRC data. In an error-free transmission, the two CRC data do not differ. If a difference is found between the CRC data transmitted by the dialysis machine and the CRC data calculated by the remote control unit, then there is obviously a transmission error. The remote control unit may then request a new transmission of the corresponding dialysis machine. If the transmission is still faulty, the remote control unit can output (optically, acoustically or haptically) an error message signal, which should prompt the medical personnel to check the respective dialysis machine.

In addition to transmission of the image content together with the data from a CRC, a time stamp may also be transmitted, providing information about the time of day to be assigned to the transmitted image content. On receiving a new image content, the remote control unit compares the new image content having the transmitted time stamp with the last received time stamp and the current time. Due to the intended periodic transmission at equidistant time intervals in normal operation, the remote control unit can determine whether the transmission received currently is what was expected in comparison with the transmission received last or whether the current transmission has arrived too soon, which would indicate a change in the screen content, for example, a change in a measured value which takes place before the normal screen update. Such transmissions can be treated in a particular manner; for example, the change in comparison with the last transmitted screen content can be identified separately, for example, by graphic emphasis such as an arrow, color emphasis, flashing or being displayed in a separate area of the output device of the remote control unit.

In the same way, the remote control unit can ascertain that an expected transmission has failed to occur. In this case the remote control unit may request a screen update from the dialysis machine in question via the network. If this screen update fails to occur, there may be an error message prompting the medical personnel to check the dialysis machine and to order additional steps if necessary.

It is equally essential to ensure that the remote control unit is operating properly and also displays the screen content transmitted by a dialysis machine properly. To do so the remote control unit may send a confirmation message to the respective dialysis machine on properly receiving a transmission, and this message may also be provided with a time stamp. If this confirmation message does not arrive or if it arrives late, this indicates problems in transmission and the dialysis machine can report corresponding error messages and/or alarm signals. Safety is further increased by the mutual checking of the transmission.

It is also essential to ensure that operator input on the remote control unit is transmitted in error-free form to the dialysis machine. This may be achieved by the fact that the dialysis machine sends a received operator input from a remote control unit back to the remote control unit before executing an action associated with the operator input such that a comparison is performed there of whether the operator input sent and that received again match one another. Depending on this comparison, a signal is sent from the remote control unit to the dialysis machine and either enables or blocks the action associated with the operator input. After executing the action associated with the operator input, the dialysis machine may send a confirmation signal to the remote control unit, indicating that the action has been performed. If there are deviations from what is expected in this sequence at any point, an alarm signal (acoustic, optical or haptic) is output at the remote control unit and/or on the dialysis machine. The medical personnel may then check the equipment, eliminate the cause of error and acknowledge the alarm.

In all possible exemplary embodiments, such data transmission protocols which are reliable with regard to confidentiality, authenticity and integrity are preferred for the transmission of data and include, for example, the Internet protocol security (IPSec) or virtual private network (VPN, OpenVPN) as the data transmission protocols.

In addition, a data transmission protocol with secure identification of the exchanging devices, such as Bluetooth or infrared (IRDA "infrared data association) can be used for authentication of the dialysis machine to be operated and of the remote control unit.

It is possible to provide that unique identification features of the communicating devices, such as MAC addresses or device identification numbers are exchanged in the initial contact between the dialysis machine to be operated and the remote control unit. These identification features may be linked to different legitimations. The data transmission may be allowed, blocked or restricted, depending on the legitimation. This procedure ensures that information is transmitted from the dialysis machine only to authorized persons.

Due to the secure identification of the dialysis machine to be operated and of the remote control unit, a single remote control unit may be used to operate multiple different dialysis machines in a simple method. This ensures that the operator at the remote control unit of the dialysis machine to be operated will be identified unambiguously, for example, by display of a device identification number.

To save energy with the dialysis machine, its touchscreen display may be switched off or operated at a reduced brightness. Only in the event of operation or when there is an alarm message is it possible to provide for the display to be operated in normal mode. The operability of the dialysis machine and the feasibility of providing information can be preserved by the inventive data transmission to a remote control unit. In a dialysis ward having a plurality of dialysis machines, a great deal of energy can be saved in this way, and this has a positive effect on the operating costs.

In all exemplary embodiments it is possible to provide that in the case of a terminated connection between the dialysis machine and the remote control unit or in the case of a defective connection the dialysis machine automatically goes into a secure operating state so as to increase safety and not endanger the patient. Such a safe state is, for example, [achieved by clamping off the extracorporeal blood circulation from the vascular system of the patient by using corresponding clamps on the arterial and venous accesses of the patient and by completely stopping the blood pump.

Another embodiment of the invention provides for alarm states which detect a dialysis machine are first transmitted to the remote control unit without leading to a direct output of an optical, acoustic or haptic alarm signal on the dialysis machine. Dialysis machines a usually equipped with a number of monitoring devices which monitor the dialysis treatment and send out alarm signals in an error case. These alarm signals may be optical, acoustic and haptic. It is essential for the alarm signals that they are noticed by the medical personnel. However, when sending out an alarm signal in a dialysis center, not only is the medical personnel alerted but also the patients who are present are disturbed by the alarm signal. To avoid this disturbance, the invention provides for an alarm state that occurs to first be signaled on the remote control unit.

The medical personnel that must approach the respective dialysis machine to eliminate the cause of the alarm is therefore alerted first. Then the medical personnel can subsequently acknowledge the alarm on the dialysis machine. It is possible to provide that the dialysis machine responds itself to a lack of acknowledgment of the alarm by delayed signaling of the alarm to the dialysis machine.

BRIEF DESCRIPTION OF THE DRAWINGS

Additional details and advantages of the invention will now be described in greater detail on the basis of the exemplary embodiments shown in the drawings, in which.

DETAILED DESCRIPTION OF THE PREFERRED EMBODIMENTS

Figure 1:
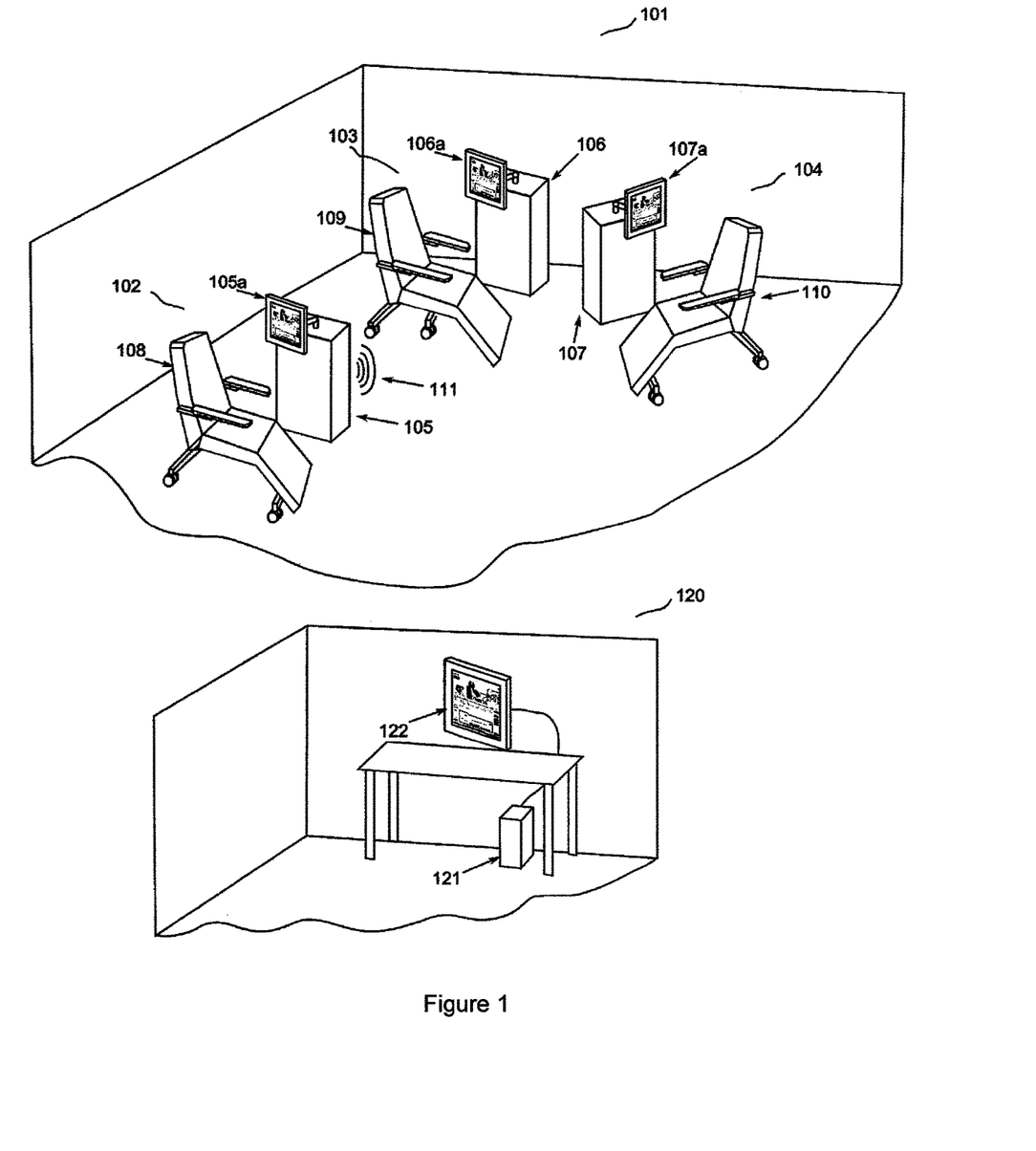
FIG. 1 shows a dialysis ward having equipment according to the invention for remote monitoring and control of dialysis machines.

FIG. 1 shows a typical dialysis ward with a treatment room 101 and a monitoring room 120 which may be located a distance apart from one another. Three treatment wards 102, 103, 104 each comprising dialysis machines 105, 106, 107 and patient seating equipment 108, 109, 110, here designed as a couch are provided in treatment room 101. The dialysis machines 105, 106, 107 are each equipped with an output device 105a, 106a, 107a, which are embodied here as a touchscreen as an example.

In monitoring room 120 a remote control unit, embodied here as a stationary computer 121 with a touchscreen 122 is provided. In the monitoring room the medical personnel has the option to monitor a patient's dialysis treatment in the remote treatment room 101 and/or to influence the control of the machine. In FIG. 1 concentric circles 111 indicate how the dialysis machine sends data to the remote control unit 121 by radio, for example, over a secured WLAN connection. The remote control unit may then display the screen content or parts thereof on its output device 122. In addition, the user interfaces of the dialysis machine 105 sending the content are displayed on the touchscreen 122. The medical personnel can operate the transmitting dialysis machine by depressing these user interfaces in the same way as if the operator input were being made on a touchscreen 105a. The remote control unit 121 therefore communicates in the manner already described with the dialysis machine 105, which converts the operator input on the remote control unit.

The dialysis machines 105, 106, 107 may be equipped with a camera and a microphone in the manner already described (not shown in FIG. 1). The camera is preferably movably mounted on the dialysis machine or on a patient interface which interacts with the dialysis machine so that it can be aligned with the patient. Alternatively, however, one or more movable cameras may also be mounted, for example, on the ceiling of the treatment room 101, which can be directed at a patient by control. It is essential that cameras with which the image of a certain patient can be sent to the remote control unit can be provided.

Figure 2:
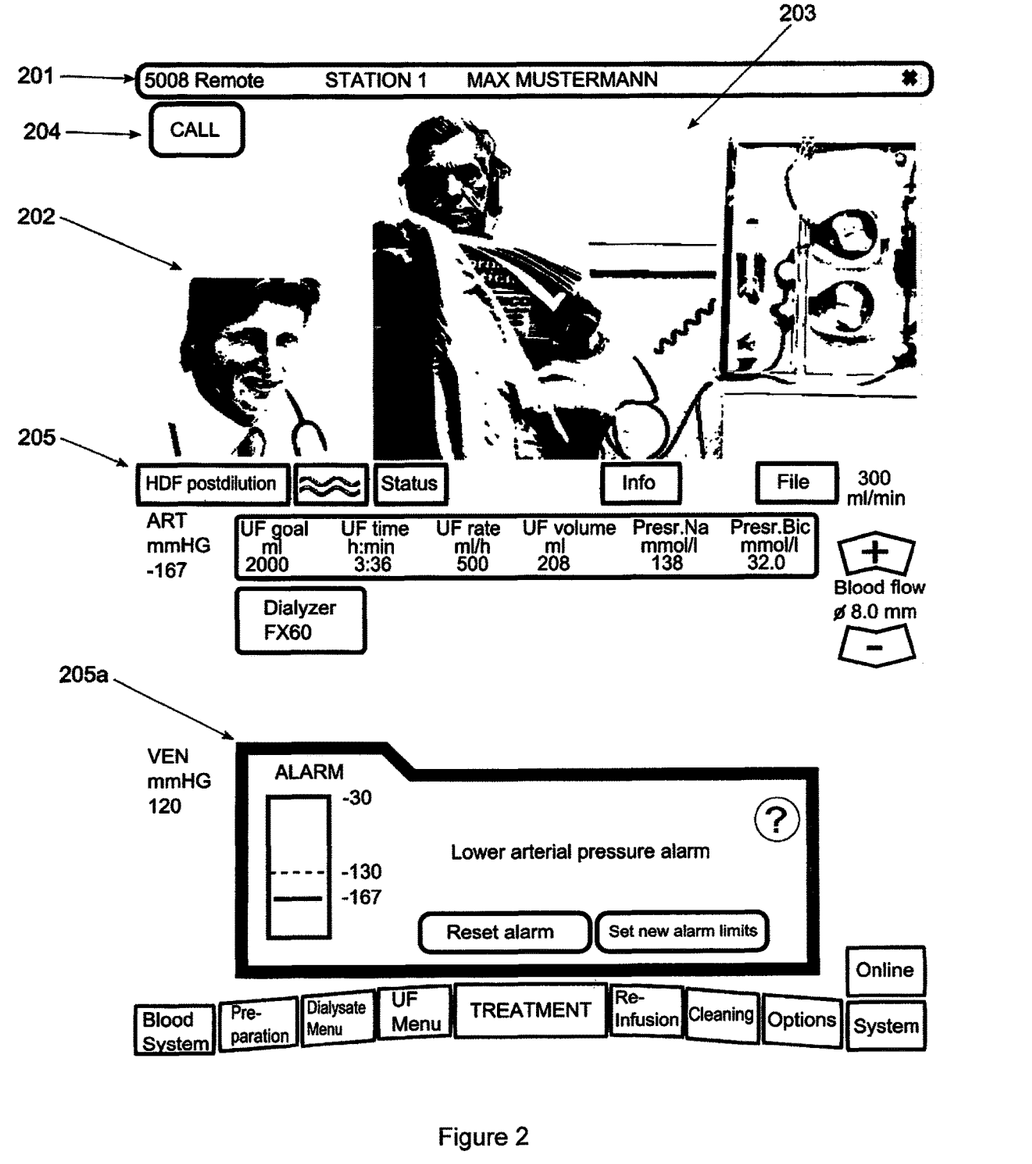
FIG. 2 shows a first embodiment of the screen content of an inventive remote control unit for remote monitoring and control of dialysis machines.

FIG. 2 shows an example of the screen content of a dialysis machine on the output device of a remote control unit.

The screen display consists of the information in a display region 201, indicating which dialysis machine (dialysis machine 5008 in FIG. 2) in which treatment room (ward 1) with which patient (Max Mustermann) is being monitored and controlled by the remote control unit at this moment. Display region 201 shows the current image 202 and 203 of the medical personnel at the remote control unit and the patient at the respective dialysis machine. An audio-visual connection between the medical personnel and the patient can be established by pressing with the finger on operator input 204 (CALL). This is done in the manner already described using cameras, loudspeaker and microphones on the dialysis machine and on the remote control unit.

Among the images of the medical personnel and the patient, the transmitted one-to-one image 205 of the screen content of the dialysis machine is displayed. This display can also be seen at the same time on the output device of the respective dialysis machine. This is the display of an alarm state namely the alarm indicating that the arterial pressure has dropped below a cutoff limit. The alarm message appears in a special region 205a of the display region 205. The medical personnel has the option of either resetting the alarm (indicated by the user interface "Reset alarm" in FIG. 2) or entering a new lower limit for the arterial pressure (represented by the user interface "Set new alarm limits" in FIG. 2). In the same way any operator input for a certain dialysis machine even those not preceded by an alarm message can be made on the remote control unit.

Furthermore an additional acoustic, optical or haptic alarm signal may also be output on the remote control unit to alert the medical personnel. This alarm signal may be suppressed on the respective dialysis machine in order not to disturb the respective patient or interfere with patients being treated in the same room.

It may happen that certain situations occur in which the medical personnel must approach a certain dialysis machine. Examples of this might be when the patient has a concern or when manual procedures are required on the machine, for example, disconnecting the patient from the dialysis machine.

Figure 3:
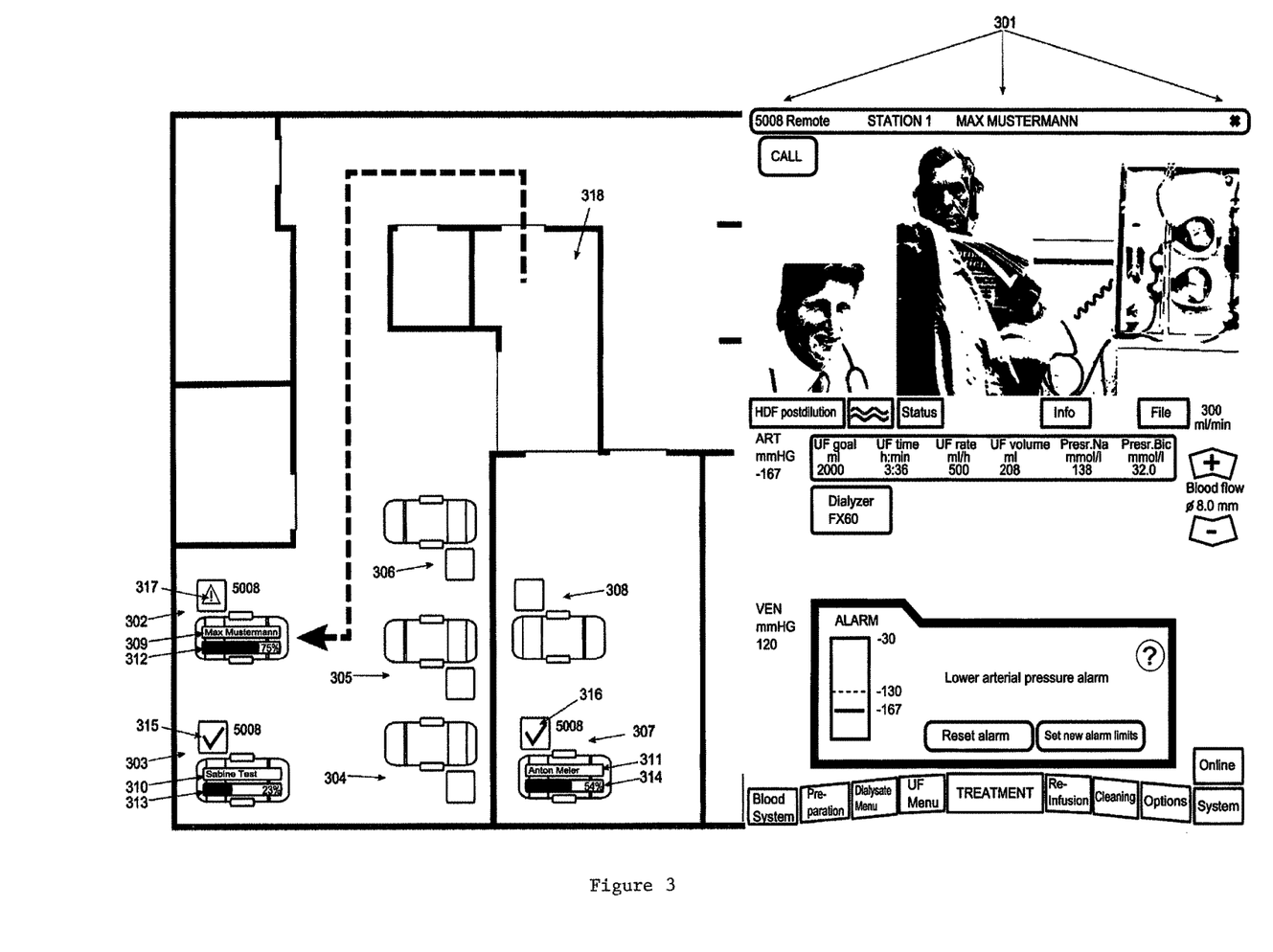
FIG. 3 shows another embodiment of the screen content of an inventive remote control unit for remote monitoring and control of dialysis machines and FIG. 4 shows an inventive remote control unit designed as a smartphone for remote monitoring and control of dialysis machines.

FIG. 3 shows how the remote monitoring and remote control of multiple dialysis machines within one dialysis ward are facilitated according to the invention. The right part 301 of FIG. 3 corresponds to the display as shown in FIG. 2. In addition, a layout of the dialysis ward is shown in the left part of FIG. 3. This gives the medical personnel an overview of how the ward is currently occupied by which patients, on which dialysis machine these patients are being treated, where these dialysis machines are located in the dialysis ward and the status of the treatment currently. The entire FIG. 3 is an example of a screen display on a remote control unit, for example, on a large monitor with a touch-screen functionality in a monitoring room of a dialysis ward.

FIG. 3 shows a view illustrating where the dialysis machines 302 to 308 are located and whether these machines are currently in use. To do so the dialysis machines with patient accommodating furnishings are shown in a layout diagram of the dialysis ward. If a patient is currently being treated on a certain dialysis machine, his name may appear in a display area (309, 310, 311) inside the patient accommodating furnishings, as symbolized here. Likewise the progress of the dialysis treatment can also be displayed. In FIG. 3 this is accomplished through bar displays 312, 313, 314 each showing the percentage of elapsed dialysis time in relation to the total dialysis time but other forms of representation are also conceivable.

Checkmarks 315, 316 are displayed in the respective symbolic dialysis machine in FIG. 3 when the treatment is proceeding within normal parameters or alarm symbols 317 appear when a problem occurs. Any other characters and displays are also conceivable. It is important only that it is signaled unambiguously to the observer whether a certain dialysis machine is currently posing a problem or whether the treatment is proceeding currently without any problem on a certain dialysis machine.

The arrow shown with an interrupted line in FIG. 3 having its origin in the monitoring room 318 and pointing to dialysis machine 302 indicates clearly to the medical personnel to which dialysis machine they must move in case of need. Moreover the arrow implements a type of pointer which makes it easier for the personnel in a large dialysis ward having a plurality of treatment sites to find a specific dialysis machine. Any graphical displays are conceivable for representing the pointer.

Figure 4:
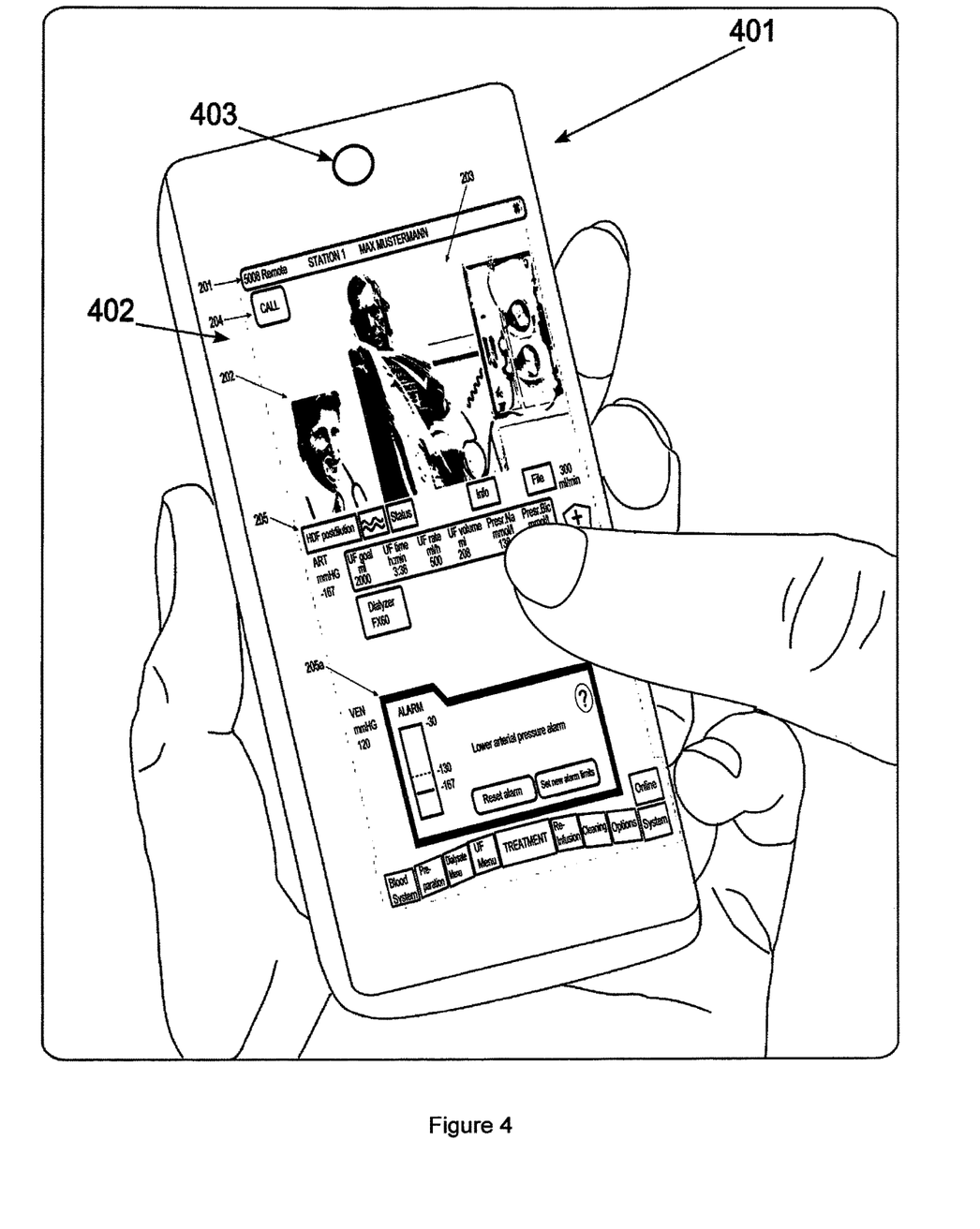
Figure 5:
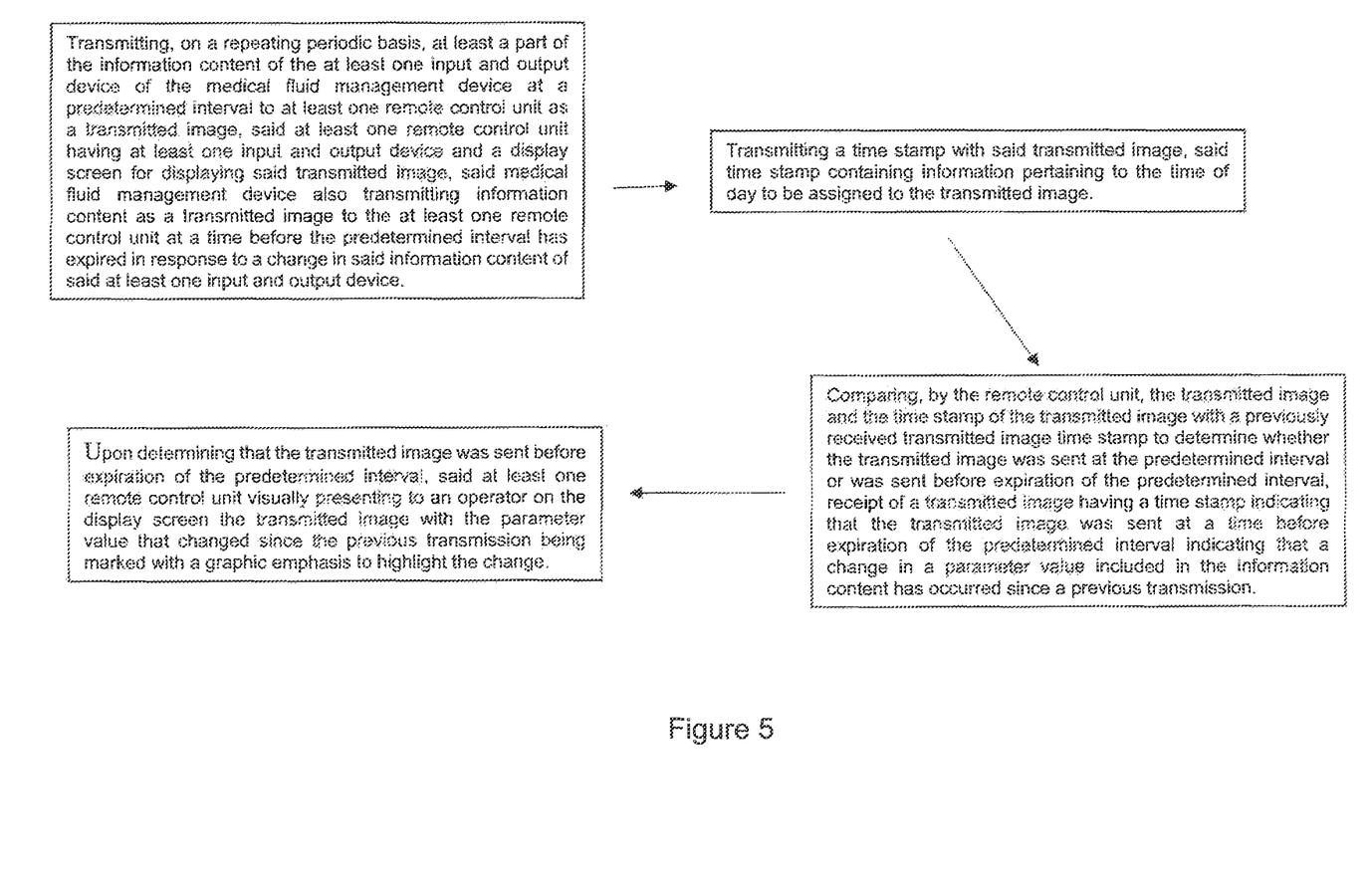
FIG. 5 shows a flow diagram of a process of the invention.

It is conceivable that the personnel additionally has a display on a portable device as shown in FIG. 4. The path to a certain dialysis ward may be represented on such a device as a function of the position of the medical personnel, much like with a navigation unit. The device thus gives the observer instructions in the form of arrows, for example, and/or acoustic directional information indicating where the observer should go to reach a specific dialysis machine. The medical personnel would thus be directed to a patient on the shortest possible path.

It is also conceivable that such a pointer may be displayed on portable devices for medical personnel who are not involved with the dialysis treatment but instead perhaps must perform medical actions on a certain dialysis patient because of another indication during a dialysis treatment. Thus, for example, in the case of a pregnant dialysis patient, an obstetrician/gynecologist may be called in case of need in which case the latter could become oriented rapidly on the basis of the pointer being displayed on a portable device such as a smartphone and can reach the patient promptly and reliably. The position determination on the remote control unit may be accomplished through methods familiar with navigation systems, for example, by using a GPS-based position determination. However, it is also conceivable to analyze the signal strengths of mobile radio or WLAN transmitters.

FIG. 4 illustrates an exemplary embodiment of a portable remote control unit 401 which is designed as a smartphone. The display 402 on a portable remote control unit does not differ fundamentally from the displays on the output devices of a stationary remote control unit. The implementation as a smartphone, however, makes it possible for medical personnel to be involved in the monitoring and control of dialysis machines even if they are not within walking distance from the dialysis machines. It is conceivable that hemodialysis patients, for example, may be monitored by medical personnel via a remote control unit in this way. It does not matter here which type of dialysis the patient is undergoing at home.

It is also conceivable that a dialysis physician, for example, might be equipped with such a portable control unit and be able to participate in the monitoring and control of dialysis machines by mobile communications network.

Such mobile control units are often equipped with a camera as shown by camera lens 403 in FIG. 4. Equipment with a loudspeaker and a microphone is standard with smartphones anyway but also with tablet PCs as another example of a portable remote control unit are usually equipped with a camera, microphone and loudspeaker. Smartphones and tablet PCs are usually equipped with touchscreens. However, it is also conceivable for the remote mobile control unit to be a laptop, notebook or netbook with a keyboard which may be equipped with a touchpad and/or a computer mouse.

Due to the mobility of the remote control unit in the embodiment shown in FIG. 4, the medical personnel can be contacted at any time and any place. It is conceivable that the normal attending medical personnel will preferably remain within walking distance of the patient in monitoring the dialyzes but dialysis physicians need not necessarily be present in walking distance from the patient. In case of need the advice of a specialist, preferably a dialysis physician and/or nephrologist may be obtained in this way. The specialist may be anywhere in the world within range of a supported mobile communications network or may use an Internet connection. Extensive options for control of the dialysis machines are available to the specialist through transmission of the screen content and the user interfaces. It is conceivable that contacting a specialist is initiated independently by a mobile remote control unit of the dialysis machine. This may occur, for example, in certain alarm situations or with certain patients who require special attention, for example, because of a special medical indication. However, contact of a specialist may also equally be done by the medical personnel.

The present invention describes methods and devices which make the sequences within a dialysis ward or in home dialysis safer, more convenient and simpler. It is clear to those skilled in the art that the methods described here can be applied not only to dialysis but also anywhere that medical technical equipment and attending personnel can interact at a distance from one another.

The invention relates to the following aspects:

1. A method for remote monitoring and control of medical fluid management equipment having at least one input and output device, preferably a touchscreen display
    characterized in that
    a data transmission takes place in which at least parts of the information content of the at least one input and output device of a medical fluid management device are transmitted and output to at least one remote control unit, and the operator entries can be input on at least one input and output device of the at least one remote control unit, preferably a touchscreen, controlling the medical fluid management device.
2. The method according to aspect 1, characterized in that the transmission of at least parts of the information content of the at least one input and output device of a medical fluid management device to at least one remote control unit takes place periodically.
3. The method according to aspect 1, characterized in that the transmission of at least parts of the information content of the at least one input and output device of a medical fluid management device to at least one remote control unit takes place immediately when the information content of the at least one input and output device of the medical fluid management device changes.
4. The method according to any one of the preceding aspects, characterized in that the change in the transmitted information content of the at least one input and output device of the medical fluid management device to the at least one input and output device of the at least one remote control unit is emphasized graphically.
5. The method according to any one of the preceding aspects, characterized in that the data transmission is provided with a time stamp, which is also transmitted.
6. The method according to any one of the preceding aspects, characterized in that a CRC check ensures that the transmission of the information content of the at least one input and output device to a remote control unit has taken place without error.
7. The method according to any one of the preceding aspects, characterized in that the data transmission between the medical fluid management device and the remote control unit takes place over a secure data transmission protocol.
8. The method according to any one of the preceding aspects, characterized in that the medical fluid management device automatically assumes a secure state when termination of a connection between the fluid management device and a remote control unit is detected.
9. The method according to any one of the preceding aspects, characterized in that the medical fluid management device is a blood treatment device.
10. The method according to aspect 9, characterized in that the blood treatment device is equipped for hemodialysis, for hemofiltration, for hemodiafiltration, for plasmapheresis or for automatic peritoneal dialysis.
11. The method according to any one of the preceding aspects, characterized in that the remote control unit is a stationary computer.
12. The method according to any one of the preceding aspects, characterized in that the remote control unit is a tablet PC.
13. The method according to any one of the preceding aspects, characterized in that the remote control unit is a smartphone.
14. The method according to any one of the preceding aspects, characterized in that the medical fluid management device and/or the remote control unit are equipped with a camera and a loudspeaker and a microphone, at least one camera image and at least one microphone signal being generated.
15. The method according to aspect 14, characterized in that a camera image and a microphone signal are transmitted from the medical fluid management device to the remote control unit and/or vice versa.
16. The method according to aspect 14, characterized in that camera images and microphone signals from at least two medical fluid management devices are exchanged between at least two medical fluid management devices.
17. The method according to any one of aspects 14 through 16, characterized in that a camera image transmitted to a medical fluid management device is displayed on a mobile patient interface.
18. The method according to any one aspects 14 through 17, characterized in that the camera image is displayed on a partial area of an output device.
19. The method according to any one of the preceding aspects, characterized in that an alarm state is transmitted from the medical fluid management device to a remote control unit and is output as an acoustic, optical or haptic alarm, at first on only the remote control unit.
20. The method according to any one of the preceding aspects, characterized in that operator input at the remote control unit receives a priority and is transmitted to the medical fluid management device.
21. The method according to aspect 20, characterized in that the operator input of a high priority is executed preferentially on the medical fluid management device in comparison with operator input of a lower priority.

22. The method according to any one of the preceding aspects, characterized in that the operating persons are authenticated on the remote control unit.

23. The method according to aspect 22, characterized in that the authentication of the operator is down by manual input of a personal alphanumeric code or by input of a fingerprint or by entering an optical iris scan.

24. The method according to any one of the preceding aspects, characterized in that a floor plan of medical fluid management devices of a treatment ward is displayed on the output device.

25. The method according to aspect 24, characterized in that the path from the remote control unit to a medical fluid management device is displayed graphically in the floor plan.

26. The method according to any one of the preceding aspects, characterized in that direction instructions indicating the path from the remote control unit to a medical fluid management device are displayed on the output device of the remote control unit.

27. A system comprising a medical fluid management device having at least one input and output device, preferably a touchscreen display and at least one remote control unit having at least one input and output device, preferably a touchscreen display, characterized in that the medical fluid management device and the remote control unit are equipped to transmit data, such that at least parts of the information content of the at least one input and output device of the medical fluid management devices are transmitted to at least one remote control unit, and the remote control unit is equipped to display the information content transmitted from the medical fluid management device on the at least one input and output device and to transmit operator input on the at least one input and output device to the medical fluid management device.

28. The device according to aspect 27, characterized in that the medical fluid management device and the remote control unit are equipped to transmit at least parts of the information content of the at least one input and output device of the medical fluid management device to at least one remote control unit periodically.

29. The device according to aspect 27, characterized in that the medical fluid management device and the remote control unit are equipped to transmit at least parts of the information content of the at least one input and output device of the medical fluid management device to at least one remote control unit immediately when the information content of the at least one input and output device of the medical fluid management device changes.

30. The device according to any one of aspects 27 to 29, characterized in that the medical fluid management device and the remote control unit are equipped to graphically emphasize a change in the transmitted information content of the at least one input and output device of the medical fluid management device on the at least one input and output device of the at least one remote control unit.

31. The device according to any one of aspects 27 to 30, characterized in that the medical fluid management device and the remote control unit are equipped to provide a time stamp for the data transmission.

32. The device according to any one of aspects 27 to 31, characterized in that the medical fluid management device and the remote control unit are equipped to perform a CRC check to ensure that the transmission of the information content of the at least one input and output device to a remote control unit has occurred without error.

33. The device according to any one of aspects 27 to 32, characterized in that the medical fluid management device and the remote control unit are equipped to have the data transmission between the medical fluid management device and the remote control unit take place via a secure data transmission protocol.

34. The device according to any one of aspects 27 to 33, characterized in that the medical fluid management device is equipped to automatically assume a secure state when termination of a connection between the fluid management device and the remote control unit is detected.

35. The device according to any one of aspects 27 to 34, characterized in that the medical fluid management device is a blood treatment device.

36. The device according to aspect 35, characterized in that the blood treatment device is equipped for hemodialysis, for hemofiltration, for hemodiafiltration, for plasmapheresis and/or automatic peritoneal dialysis.

37. The device according to any one of aspects 27 to 36, characterized in that the remote control unit is a stationary computer.

38. The device according to any one of aspects 27 to 37, characterized in that the remote control unit is a tablet PC.

39. The device according to any one of aspects 27 to 38, characterized in that the remote control unit is a smartphone.

40. The device according to any one of aspects 27 to 39, characterized in that the medical fluid management device and/or the remote control unit is/are equipped with a camera and a loudspeaker and a microphone, at least one camera image and at least one microphone signal being generated.

41. The device according to aspect 40, characterized in that the medical fluid management device and the remote control unit are equipped to transmit a camera image and a microphone signal from the medical fluid management device to the remote control unit and/or vice versa.

42. The device according to any one of aspects 40 to 41, characterized in that the medical fluid management device is equipped to receive a camera image and a microphone signal from at least one additional medical fluid management device.

43. The device according to any one of aspects 40 to 42, characterized in that it comprises a mobile patient interface equipped to display a camera image.

44. The device according to any one of aspects 40 to 43, characterized in that the medical fluid management device and/or the remote control unit is/are equipped to display a camera image on a partial area of an output device.

45. The device according to any one of aspects 27 to 44, characterized in that the medical fluid management device is equipped to transmit an alarm state to a remote control unit and to suppress the output of an acoustic, optical or haptic alarm temporarily.

46. The device according to any one of aspects 27 to 45, characterized in that the remote control unit is equipped to provide operator input with a priority and to transmit the operator input to a medical fluid management device.

47. The device according to aspect 46, characterized in that the medical fluid management device is equipped to execute operator input of a high priority preferentially in comparison with operator input of a lower priority.

48. The device according to any one of aspects 27 to 47, characterized in that the remote control unit is equipped so that the operating persons on the remote control unit authenticate themselves.

49. The device according to aspect 48, characterized in that the remote control unit is equipped to enable the authentication by manual input by an operator of a personal alphanumeric code or by entering a fingerprint of the operator or by entering an optical iris scan.

50. The device according to any one of aspects 27 to 49, characterized in that the remote control unit is equipped to display a floor plan of medical fluid management devices of a treatment ward on the output device of the remote control unit.

51. The device according to aspect 50, characterized in that remote control unit is equipped to display graphically the path from the remote control unit to the medical fluid management device in the floor plan.

52. The device according to any one of aspects 27 to 51, characterized in that the remote control unit is equipped to display direction instructions on the output device of the remote control unit, showing the path from the remote control unit to the medical fluid management device.

53. The medical fluid management device implemented with the features of at least one of aspects 27 to 52.

54. The control unit implemented with the features of at least one of aspects 27 to 52.

The invention claimed is:

1. A medical system comprising:
multiple medical devices, wherein each of the medical devices is positioned at a respective location and comprises a respective display device; and
a first remote device configured to:
communicate with the multiple medical devices to determine respective locations and respective treatment states of medical treatments that the medical devices are providing, and to transmit, to the medical devices, identification information authenticating the first remote device,
receive, from a particular medical device in the multiple medical devices, one or more images of at least a portion of a screen content presented on a display device of the particular medical device, the portion of the screen content including an alarm indicator indicating a state of an alarm on the particular medical device, wherein the particular medical device sends the one or more images in response to authenticating the first remote device based on the identification information,
display on a user interface of the first remote device (i) the one or more images of the screen content of the particular medical device, (ii) the respective locations of the multiple medical devices, and (iii) the respective treatment states of the multiple medical devices, and
transmit, to the particular medical device, first data that influences control of the particular medical device, wherein the first data comprises command signals for altering the state of the alarm of the particular medical device, and wherein the first data comprises high priority command signals,
wherein the particular medical device is configured to:
receive, from a second remote device, second data that influences the particular medical device, the second data comprising low priority command signals, and
preferentially perform operations in accordance with the high priority command signals with respect to the low priority command signals.

2. The medical system of claim 1, wherein the first remote device comprises a computing device and a touchscreen.

3. The medical system of claim 1, wherein the first remote device comprises a mobile computing device.

4. The medical system of claim 1, wherein the particular medical device comprises an interface wirelessly connected to a remote server.

5. The medical system of claim 1, wherein the first remote device communicates with the multiple medical devices through a short-range wireless technology protocol that comprises one or more of wireless local area network communications or infrared communications.

6. The medical system of claim 1, wherein the display device of the particular medical device comprises a touchscreen.

7. The medical system of claim 1, wherein the particular medical device comprises a dialysis machine.

8. The medical system of claim 1, wherein the one or more images further comprise an image of a user of the particular medical device.

9. The medical system of claim 8, wherein the particular medical device further comprises a camera, wherein the image of the user is captured by the camera.

10. The medical system of claim 1, wherein at least a portion of the user interface of the first remote device displays one or more images of a user of the particular medical device.

11. The medical system of claim 1, wherein the at least a portion of the screen content comprises values representing one or more settings of the particular medical device.

12. The medical system of claim 11, wherein the settings comprise a dialysis fluid flow rate.

13. The medical system of claim 1, wherein the first data that influences the particular medical device comprises command signals for ceasing a dialysis treatment.

14. The medical system of claim 1, wherein:
the screen content comprises one or more images of a user of the first remote device; and
the first remote device is further configured to:
capture, using a camera of the first remote device, the one or more images of the user of the first remote device; and
transmit, to the particular medical device, the one or more images of the user of the first remote device for display on the display device.

15. The medical system of claim 1, wherein the first data comprises the command signals for altering a dialysis fluid flow rate of the particular medical device.

16. The medical system of claim 1, wherein a respective treatment state of each medical device indicates a progress of the medical treatment that the medical device is currently providing to a patient, and wherein a treatment state of a first medical device in the multiple medical devices is different from a treatment state of a second medical device in the multiple medical devices.

17. The medical system of claim 1, wherein a treatment state of a first medical device indicates that the first medical device needs attention, and wherein the first remote device is further configured to display one or more indicators that point out to the first medical device that needs attention such that the first medical device is distinguished from medical devices that do not need attention.

* * * * *